(12) United States Patent
Lee

(10) Patent No.: US 7,087,038 B2
(45) Date of Patent: Aug. 8, 2006

(54) LOCKING SYSTEM FOR CATHETER

(76) Inventor: Nak-Ho Lee, Sungwon Medical, 170-10, Beeha-Dong, Heungduck-Gu, Chungbuk, Cheongju (KR) 361-825

( * ) Notice: Subject to any disclaimer, the term of this patent is extended or adjusted under 35 U.S.C. 154(b) by 13 days.

(21) Appl. No.: 10/513,783

(22) PCT Filed: May 18, 2002

(86) PCT No.: PCT/KR02/00939

§ 371 (c)(1),
(2), (4) Date: Nov. 16, 2004

(87) PCT Pub. No.: WO03/097127

PCT Pub. Date: Nov. 27, 2003

(65) Prior Publication Data

US 2005/0203485 A1  Sep. 15, 2005

(51) Int. Cl.
*A61M 37/00* (2006.01)
(52) U.S. Cl. .................... 604/95.04; 604/523; 604/533
(58) Field of Classification Search ............ 604/95.01, 604/95.04, 533, 523, 535, 540, 541; 607/115–120
See application file for complete search history.

(56) References Cited

U.S. PATENT DOCUMENTS

| | | | |
|---|---|---|---|
| 4,586,923 A | | 5/1986 | Gould et al. |
| 4,643,720 A | * | 2/1987 | Lanciano ................. 604/95.04 |
| 5,397,321 A | | 3/1995 | Houser et al. |
| 5,399,165 A | | 3/1995 | Paul, Jr. |
| 5,599,291 A | * | 2/1997 | Balbierz et al. ................ 604/8 |
| 5,928,208 A | * | 7/1999 | Chu et al. .................... 604/523 |
| 5,941,849 A | * | 8/1999 | Amos et al. ............. 604/95.04 |
| 5,989,241 A | * | 11/1999 | Plishka et al. .............. 604/540 |
| 6,159,177 A | * | 12/2000 | Amos et al. ............. 604/95.04 |
| 6,454,740 B1 | * | 9/2002 | Mody ...................... 604/95.04 |
| 6,508,789 B1 | * | 1/2003 | Sinnott et al. ......... 604/164.02 |
| 6,673,060 B1 | * | 1/2004 | Fleming, III ................ 604/540 |
| 6,699,233 B1 | * | 3/2004 | Slanda et al. ............... 604/533 |
| 2005/0107739 A1 | * | 5/2005 | Palma ........................ 604/104 |

FOREIGN PATENT DOCUMENTS

| | | |
|---|---|---|
| JP | 6-238003 | 8/1994 |
| JP | 7-080077 | 3/1995 |

OTHER PUBLICATIONS

English Language Abstract of JP7-080077.

* cited by examiner

*Primary Examiner*—Cris Rodriguez
(74) *Attorney, Agent, or Firm*—Greenblum & Bernstein, P.L.C.

(57) ABSTRACT

A catheter of the present invention includes a tubular member and a lockable connector having a hub and a locking device. The locking device includes a semi-oval button; a rectangular main operating part; an accepting part having a pair of projections and an accepting hole; and a latching part coupled to one of the projections. The hub includes a guide hole into which the locking device is inserted and a first body passage formed horizontally toward the inside of the hub, the first body passage communicating with the guide hole. The locking device can be released from the locked position only by use of an appropriate key. A tip of the tubular member is made of hard material and has a double adhesion structure so that the catheter tube can easily be inserted into a body cavity.

2 Claims, 4 Drawing Sheets

LOCKING SYSTEM FOR CATHETER

TECHNICAL FIELD

The present invention relates to catheters and, more particularly, to a drainage catheter having a locking device which can be locked or unlocked more easily. In addition, the present invention relates to a distal end of catheter made of hard material so that the drainage catheter can easily be inserted into a body cavity.

BACKGROUND ART

Drainage catheters are generally used to drain bile or pus from a body cavity, for example, an abdominal cavity in order to mitigate symptoms of diseases. A Drainage catheter comprises a tubular member having a proximal end opposite a distal end, a tension member, and a lockable connector. The tubular member includes a series of holes positioned proximate the distal end. The distal end of the tubular member is formed to be positioned into a desired configuration such as a closed loop or pigtail. The tension member extends through the hollow tubular member and is positioned for drawing the distal end into the desired configuration. The lockable connector comprises a hub coupled to the proximal end of the tubular member and a locking lever coupled to the hub. The locking lever secures the pulling end of the tension member to the hub after the tension member is fully pulled so that the desired loop configuration can be maintained. The hub has a coupling end, through which a channel extends. The channel is aligned with and connected to the tubular member by a connector cap.

FIG. 1 shows a cam-locked drainage catheter, as a conventional drainage catheter, which can adjust arbitrarily a loop configuration of a distal end (10') of a tubular member (1'). The cam-locked drainage catheter comprises a lockable connector (2') having a hub and a locking lever (21') pivotedly connected in a channel of the hub for moving a cam surface at one end of the lever between a locked position and an unlocked position. Thus, a patient can easily use the drainage catheter with one hand. These catheters are typically introduced into the patient by means of a large hypodermic needle or trocar. A wire guide is inserted through the needle, which is then removed. The tubular member (1') with a stiffening cannula positioned therein is then passed over the wire guide into a body cavity. The cannula and wire guide are withdrawn, leaving the catheter in the desired cavity. Then, a proximal end of a monofilament (4') as a tension member is moved or drawn to form the distal end (10') into a desired loop or pigtail configuration. Next, the locking lever (21') is pulled downward to fix the position of the monofilament with respect to the tubular member, thereby maintaining the desired loop configuration. Here, the protruding end of the monofilament (4') may be cut so as to get an appropriate length. When the locking lever (21') is pulled upward, the lever rotates by appropriate angles and the monofilament is released automatically from the locking lever (21'), thereby releasing the pigtail configuration. In addition, the loop configuration of the flexible distal end can be reformed into another configuration after straightening the distal end portion by inserting the stiffening cannula into the catheter tube.

The conventional cam-locked drainage catheters have the pivotable locking lever to hold the monofilament in place so that the loop configuration is maintained through its intended use, and, therefore, doctors can easily lock or unlock the lockable connector (2') of the catheter. However, the lever (21') may be rotated arbitrarily due to movement of a patient or inadvertences during operation, and, therefore, the monofilament may move distally and release the pigtail configuration. In addition, because a tip of the catheter tube is made of flexible (or soft) material such as polyamide, it is difficult to insert the catheter tube into a blood vessel.

DISCLOSURE OF INVENTION

Accordingly, the present invention is directed to a drainage catheter with a locking device that substantially obviates one or more problems due to limitations and disadvantages of the related art.

An object of the present invention is to provide a drainage catheter with a locking device, which can easily form the distal end of the catheter tube into the desired configuration, prevent the loop configuration of the distal end from being inadvertently released during operation, and easily release a locked position of the locking device.

Another object of the present invention is to provide a drainage catheter that can be easily inserted into a body cavity.

To achieve the object and other advantages and in accordance with the purpose of the invention, as embodied and broadly described herein, the present invention provides a drainage catheter comprising a tubular member and a lockable connector having a hub and a locking device. The locking device comprises a semi-oval button; a rectangular main operating part extending vertically from the center of the button; an accepting part having a pair of projections and an accepting hole, which accepts the main operating part; and a latching part coupled to the top of the projection with an appropriate angle. The hub comprises a guide hole into which the locking device is inserted and a first body passage formed horizontally toward the inside of the hub, the first body passage communicating with and being at right angle to the guide hole. In addition, a tip of the tubular member has a double adhesion structure so that the catheter tube can easily be inserted into a body cavity.

It is to be understood that both the foregoing general description and the following detailed description of the present invention are exemplary and explanatory and are intended to provide further explanation of the invention as claimed.

BRIEF DESCRIPTION OF THE DRAWINGS

Further objects and advantages of the invention can be more fully understood from the following detailed description taken in conjunction with the accompanying drawings, in which.

<Reference>

Figure 1:
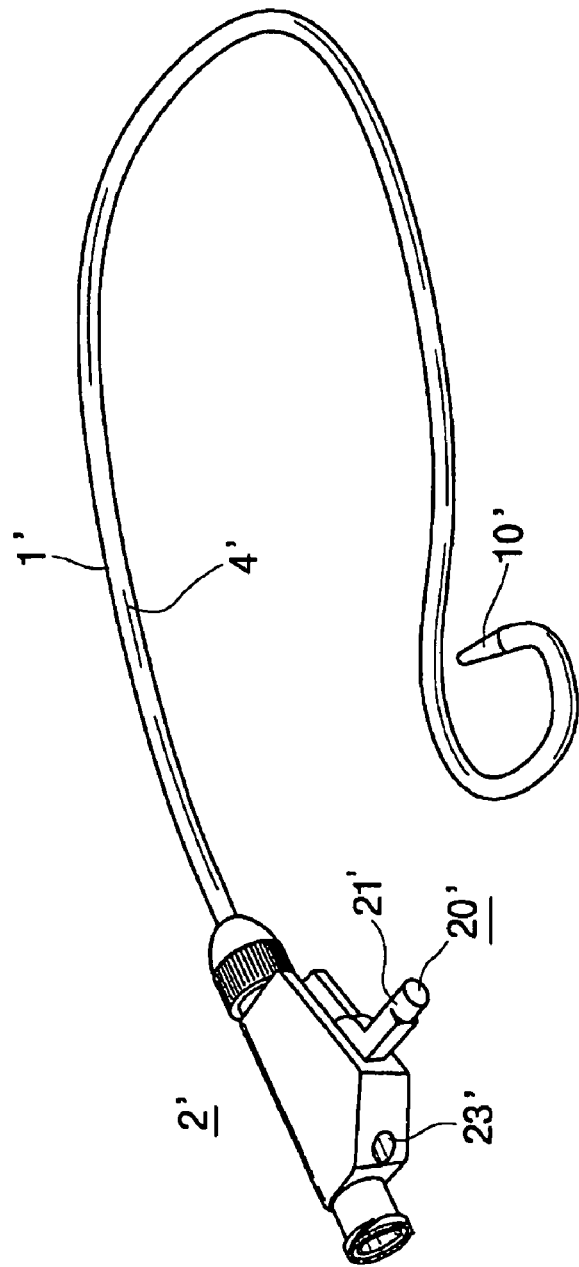
FIG. 1 depicts a conventional drainage catheter having a locking lever.

1: catheter tube
2: lockable connector

-continued

<Reference>

4: monofilament
10: a distal end of catheter tube
20: locking device
23: first body passage
24: second body passage
25: third body passage
26: guide hole
27: input hole
210: button
230: accepting part
240: main operating part
260: latching part

BEST MODE FOR CARRYING OUT THE INVENTION

Reference will now be made in detail to the preferred embodiments of the present invention, examples of which are illustrated in the accompanying drawings.

Figure 2:
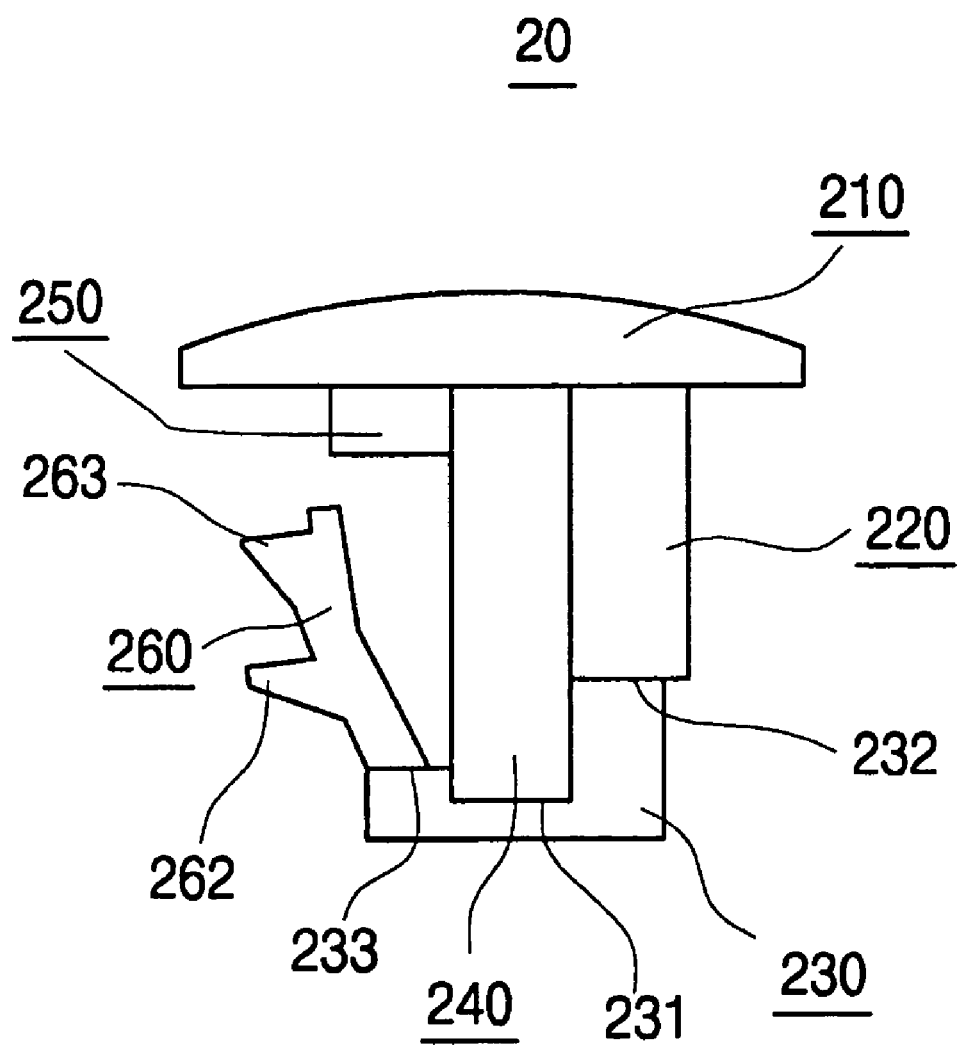
FIG. 2 depicts a cross-sectional view of the locking device according to the present invention.

Referring to FIG. 2, a locking device of the present invention comprises a semi oval button (210). The button is coupled to a main operating part (240) with a rectangular shape. On the right side of the main operating part (240), a sub-operating part (220) is positioned alongside of the main operating part. On the left side of the main operating part (240), an arrival guide part (250) about ⅙ in length of the main operating part (240) is positioned alongside of the main operating part. The distal end of the main operating part (240) is inserted into an accepting hole (231) of an accepting part (230). The accepting part (230) has a pair of projections (232 and 233) at both sides, one of which is longer than the other one. The top of the longer projection (232) is in contact with the bottom of the sub-operating part (220). A latching part (260) is coupled to the shorter projection (233) and is tilted slightly toward outside with respect to the projection (233). The latching part (260) has a first catching prominence (262) and a second catching prominence (263) that is positioned above from the first catching prominence. The first catching prominence (262) is larger in area than the second catching prominence (263).

Figure 3:
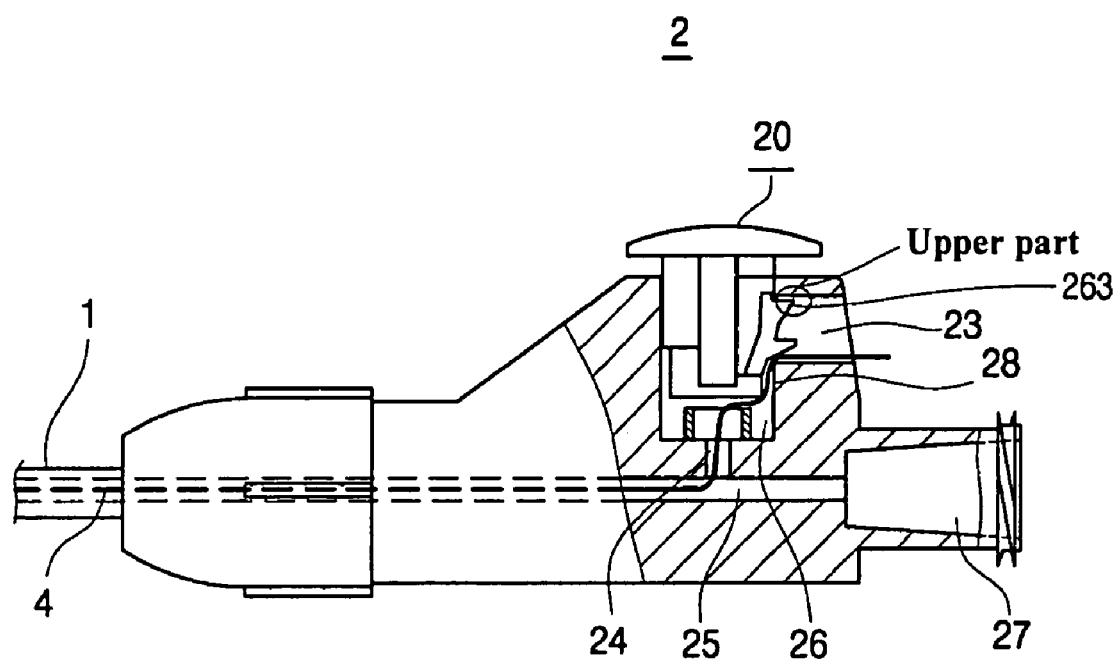
FIG. 3 depicts a sectioned longitudinal view of a hub coupled to the locking device according to the present invention.

FIG. 3 shows a partially sectioned, longitudinal view of a hub coupled to a locking device, which is in locked position. Referring to FIG. 3, the hub (2) according to the present invention comprises a first body passage (23), a second body passage (24), a third body passage (25), a guide hole (26), and an input hole (27). The first body passage (23) is formed horizontally toward the inside of the hub. The guide hole (26) is formed vertically in the hub. The guide hole (26) communicates with the first body passage (23) and is at right angle to it. The second body passage (24) is formed vertically downward from the center of the bottom of the guide hole (26). The input hole (27) projects toward outside from the hub and is coupled to the third body passage (25) horizontally. In other word, the input hole (27) communicates with the third body passage (25). The locking device (20) is inserted into the guide hole (26) of the hub.

As shown in FIG. 3, a tubular member (1) of the catheter is coupled to the hub (2) through a threaded distal connector end and a connector cap. A monofilament (4) extends through the hollow tubular member (1) via the first body passage (23), a gap (28) between the locking device (20) and the guide hole (26), the second body passage (24), and the third body passage (25). The third body passage (25) is connected to the tubular member (1) through the distal connector end so that the monofilament (4) can extend through the tubular member.

Figure 4:
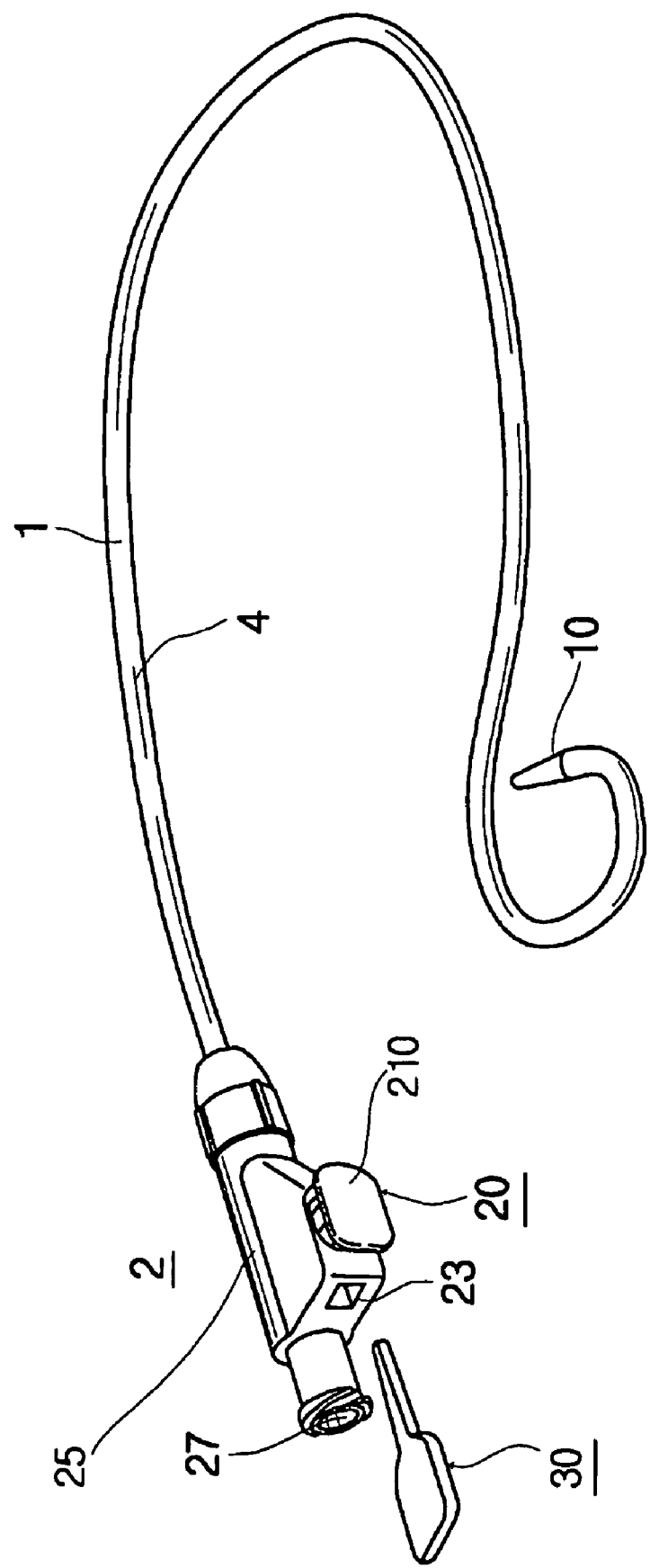
FIG. 4 depicts a drainage catheter having a lockable connector according to the present invention.

FIG. 4 depicts a drainage catheter having a lockable connector according to the present invention.

When a doctor treats a patient using the catheter according to the present invention, the doctor first determines an appropriate location on an affected part where the distal end of the catheter is positioned, and a catheter tract. After narcotizing and incising the affected part, the doctor prepares to insert the catheter into the incised part. A large hypodermic needle or trocar is introduced into the patient, and a wire guide is inserted through the needle, which is then removed. A stiffening cannula is inserted into the tubular member (1) via the input hole (27) and the third body passage (25). To perform imaging diagnosis, an adequate liquid is inputted using, for example, a trocar method. The tubular member with the stiffening cannula positioned therein is passed over the wire guide into the cavity. The cannula and wire guide are withdrawn, leaving the catheter in the desired cavity.

Then, the monofilament is drawn to configure the distal end of the catheter tube into a desired configuration. The pigtail loop of the catheter is tightened by pulling on the proximal end of the monofilament, which extends through the catheter. The desired configuration of the catheter tube can be formed through performing this procedure repeatedly. Subsequently, after forming the desired configuration, the button (210) of the locking device (20) is pressed to fix the position of the monofilament with respect to the tubular member, thereby maintaining the desired loop configuration. When the button (210) is pressed, the locking device (20) moves downward along the guide hole (26) of the hub until the second catching prominence (263) of the latching part (260) is caught on the upper part of the first body passage (23) of the hub (2). When the second catching prominence (263) is caught on the upper part of the first body passage (23), the monofilament is held in place because the gap (28) between the locking device (20) and the guide hole (26) becomes narrow. As a result, when the locking device (20) is in a locked position, the monofilament (4) is immovable, thereby maintaining the desired loop configuration.

To release the locked position of the locking device (20) in order to adjust the loop configuration, an appropriate key is used. If a user inserts the appropriate key (30) into the first body passage (23) and pushes down the latching part (260) of the locking device (20) strongly, the latching part (260) gets bent backward and, therefore, the second catching prominence (263) becomes apart from the upper part of the first body passage (23). Accordingly, the locking device (20) is released from the locked position.

In using the drainage catheter of the present invention, the locking device (20) can be released from the locked position only by means of an appropriate key (30). Thus, the doctor can treat securely the patient ensuring the locked position of the catheter, and prevent the locked position from being inadvertently released during operation by movement of the patient.

In addition, the tip of the tubular member (1) of the catheter is made of polyurethane and formed through double adhesion processing so that in inserting the catheter into a body cavity, the stiffening cannula may not deviate from the distal end (10) of the catheter tube.

INDUSTRIAL APPLICABILITY

Thus, a lockable drainage catheter according to the present invention can maintain a desired loop configuration of catheter and easily release the locked position of the catheter. Particularly, the lockable catheter with the locking device can be conveniently used as medical implement or medical equipment because it can save doctors' trouble during operation on an affected part.

What is claimed is:

1. A catheter comprising:

a tubular member;

a locking device comprising a semi-oval button, a main operating part which extends vertically from the center of said button, said main operating part having a rectangular shape, an accepting part which has a pair of projections and an accepting hole which accepts said main operating part, and a latching part coupled to one of said projections, said latching part being tilted slightly toward outside with respect to said projection; and a hub comprising a guide hole into which said locking device is inserted, and a first body passage formed horizontally toward the inside of said hub, said first body passage being at right angle to said guide hole and communicating with said guide hole.

2. The catheter of claim 1, wherein a tip of said tubular member is made of polyurethane.

* * * * *